United States Patent
Konigsmann et al.

(10) Patent No.: US 8,809,588 B2
(45) Date of Patent: Aug. 19, 2014

(54) METHOD FOR PRODUCING AROMATIC AMINES

(75) Inventors: Lucia Konigsmann, Stuttgart (DE); Ekkehard Schwab, Neustadt (DE); Michael Hesse, Worms (DE); Christian Schneider, Mannheim (DE); Thomas Heidemann, Viernheim (DE); Celine Liekens, Antwerp (BE); Jutta Bickelhaupt, Fraenkisch-Crumbach (DE); Dirk Theis, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 3 days.

(21) Appl. No.: 13/320,384

(22) PCT Filed: May 5, 2010

(86) PCT No.: PCT/EP2010/056056
§ 371 (c)(1),
(2), (4) Date: Nov. 14, 2011

(87) PCT Pub. No.: WO2010/130604
PCT Pub. Date: Nov. 18, 2010

(65) Prior Publication Data
US 2012/0065431 A1    Mar. 15, 2012

(30) Foreign Application Priority Data

May 14, 2009  (EP) .................................... 09160263

(51) Int. Cl.
*C07C 209/00*  (2006.01)
(52) U.S. Cl.
USPC ........................................................ 564/423
(58) Field of Classification Search
None
See application file for complete search history.

(56) References Cited

U.S. PATENT DOCUMENTS

| | | |
|---|---|---|
| 3,347,798 A | 10/1967 | Baer et al. |
| 2004/0147783 A1 | 7/2004 | Vanoppen et al. |
| 2010/0267551 A1 | 10/2010 | Kotrel et al. |
| 2010/0274008 A1 | 10/2010 | Kubanek et al. |
| 2010/0274009 A1 | 10/2010 | Kubanek et al. |
| 2010/0274010 A1 | 10/2010 | Kubanek et al. |
| 2010/0274011 A1 | 10/2010 | Kubanek et al. |
| 2010/0274055 A1 | 10/2010 | Kubanek et al. |
| 2011/0054167 A1 | 3/2011 | Kubanek et al. |
| 2011/0118110 A1 | 5/2011 | Kotrel et al. |

FOREIGN PATENT DOCUMENTS

| | | |
|---|---|---|
| CN | 1634860 | 7/2005 |
| CN | 1657162 | 8/2005 |
| DE | 1 127 904 | 4/1962 |
| DE | 1 278 411 | 9/1968 |
| DE | 1 442 567 | 11/1968 |
| DE | 101 24 600 | 11/2002 |
| DE | 10 2004 006 104 | 8/2005 |
| DE | 10 2006 007 619 | 8/2007 |
| EP | 1 882 681 | 1/2008 |
| EP | 1 935 871 | 6/2008 |
| WO | 2008 034770 | 3/2008 |

OTHER PUBLICATIONS

U.S. Appl. No. 13/383,014, filed Jan. 9, 2012, Kubanek, et al.
U.S. Appl. No. 13/383,321, filed Jan. 10, 2012, Kubanek, et al.
International Search Report Issued May 26, 2011 in PCT/EP10/056056 Filed May 5, 2010.
U.S. Appl. No. 13/148,595, filed Aug. 9, 2011, Wigbers, et al.
U.S. Appl. No. 13/148,409, filed Aug. 8, 2011, Wigbers, et al.
U.S. Appl. No. 13/318,257, filed Oct. 31, 2011, Steinmetz, et al.
U.S. Appl. No. 13/186,592, filed Jul. 20, 2011, Schneider, et al.

*Primary Examiner* — Clinton Brooks
(74) *Attorney, Agent, or Firm* — Oblon, Spivak, McClelland, Maier & Neustadt, L.L.P.

(57) ABSTRACT

The invention relates to a process for preparing aromatic amines by catalytically hydrogenating the corresponding aromatic nitro compound, which comprises using a copper catalyst with a support comprising $SiO_2$, the $SiO_2$ having been prepared by wet grinding and subsequent spray drying.

16 Claims, No Drawings

METHOD FOR PRODUCING AROMATIC AMINES

CROSS REFERENCE TO RELATED APPLICATIONS

This application is a 35 U.S.C. §371 national stage patent application of international patent application PCT/EP10/056,056, filed May 5, 2010, the text of which is incorporated herein by reference, and claims priority to European patent application 09160263.1, filed May 14, 2009, the text of which is also incorporated herein by reference.

The invention relates to a process for preparing aromatic amines, especially aniline, using copper catalysts on $SiO_2$ supports.

Processes for preparing aromatic amines such as aniline by hydrogenating the corresponding nitro compounds have already been known for some time. WO 2008/034770 relates to a process for preparing aromatic amines in a fluidized bed reactor. In this process, a gaseous reaction mixture comprising the nitro compound and hydrogen flows from the bottom upward through a heterogeneous particulate catalyst which forms a fluidized bed. In the fluidized bed are provided internals which in turn comprise the catalyst, the internals having a specific geometry. The catalysts used may be either supported or unsupported catalysts which comprise heavy metals of groups 1 and/or 5 to 8 of the periodic table of the elements (PTE), especially one or more of the elements copper, palladium, molybdenum, tungsten, nickel or cobalt. With regard to the support optionally present, however, there is no additional information.

CN-A 1 657 162 relates to a fluidized bed catalyst for preparing aniline by hydrogenating nitrobenzene. The catalyst comprises $SiO_2$ as a support and copper, chromium, molybdenum, and also a further metal selected from nickel, zinc, barium, vanadium, bismuth, lead or palladium. The aforementioned metals are present in oxide form in a specific weight ratio in the catalyst. The aforementioned metals are already introduced into the process in the course of preparation of $SiO_2$ in the form of aqueous salt solutions; the metals are, in contrast, not applied to the already finished support.

A process for preparing aromatic amines such as aniline by hydrogenating the corresponding nitroaromatics by means of hydrogen over fixed catalysts under adiabatic conditions is described in EP-A 1 882 681. Suitable catalysts are in principle all catalysts usable for the gas phase hydrogenation of nitro compounds. The metal component of the catalysts may be present either in the form of an alloy or as the mixed oxide, and the catalyst can optionally be prepared using an inert support material. Useful support materials include, for example, aluminum oxide (α and γ polymorph), $SiO_2$, $TiO_2$, laterite, waterglass or graphite. The metals used are preferably Pd, Te, V, Nb, Ta, Cr, Mo, W, Pb or Bi. Preference is given to using α-aluminum oxide with a BET surface area of less than 10 $m^2/g$.

EP-A 1 935 871 and DE-A 10 2006 007 619 relate primarily to the purification of aniline which has been prepared by hydrogenation of nitrobenzene in the presence of catalysts. The purification can be effected by specific distillation processes or extraction with aqueous alkali metal hydroxide solution. Suitable catalysts are, for example, those which comprise metals of transition group 8 of the PTE and which are optionally applied to support materials such as carbon or oxides of magnesium, aluminum and/or silicon. Suitable catalysts are, for example, Raney cobalt or Raney nickel catalysts. Additionally suitable are fixed heterogeneous supported catalysts such as Pd on aluminum oxide or carbon supports.

CN-A 1 634 860 relates to a gas distributor in a fluidized bed reactor, which is incorporated into a fluidized bed reactor in the synthesis of aniline. The gas distributor comprises various jet directions, the main gas inlet conduit being connected to the center of a crossed branched conduit, while a ring conduit for gas distribution is divided into 1 to 10 circles and connected to the branched conduit. In the fluidized bed reactor, a support metal catalyst with a mean particle size of 45 to 300 μm is used, the static fill height of the catalyst being two to ten times the reactor diameter. The catalyst comprises copper as the main active component, and $SiO_2$ or $Al_2O_3$ are used as supports.

Processes for producing support materials for catalysts, for example from silicon dioxide ($SiO_2$), have been known for some time (sol-gel process). A specific process for preparing supported catalysts is disclosed in DE-A 10 2004 006 104. In this process, a hydrogel is first prepared, which is then ground to fine particulate hydrogel, from which, in turn, a slurry based on the fine particulate hydrogel is obtained. Subsequently, the slurry is spray-dried to obtain the catalyst support. At least one transition metal and/or at least one transition metal compound is applied to the catalyst support. In principle, all transition metals are suitable, including copper, nickel, platinum, palladium, nickel, iron, chromium or titanium. The catalysts are used for polymerization and/or copolymerization of olefins; from the olefins, it is possible in turn to produce fibers, films and/or moldings. The use of the catalysts for preparing aniline in a hydrogenation process is, however, not described in DE-A 10 2004 006 104.

The problem underlying the present invention consists in providing a novel, economically viable process for preparing aromatic amines, especially aniline.

The object is achieved by a process for preparing aromatic amines by catalytically hydrogenating the corresponding aromatic nitro compound, which comprises using a copper catalyst with a support comprising $SiO_2$, the $SiO_2$ having been prepared by wet grinding and subsequent spray drying.

The process according to the invention has the advantage that aromatic amines, especially aniline, can be prepared with high yield and/or high chemical purity. Moreover, the process according to the invention can be performed in a very simple manner in process technology terms. An additional advantage is that the wet grinding which is performed before the spray drying produces a catalyst support which is mechanically very stable. The catalysts used in the process according to the invention are notable for high abrasion resistance. A high abrasion resistance in turn results in a prolonged catalyst lifetime. The catalyst can thus be used for a prolonged period in the hydrogenation of aromatic nitro compounds to obtain aromatic amines, the conversion of and/or the selectivity for aromatic amines remaining constant over a prolonged period or decreasing only insignificantly.

A particularly abrasion-resistant catalyst is produced when an aqueous alkali metal hydroxide is added during or after the wet grinding. The support material obtained has fewer cracks than support material (particles) with no addition of aqueous alkali metal hydroxide solution, but instead with performance of a drying and/or calcination step after the wet grinding.

The process according to the invention for preparing aromatic amines is described in detail hereinafter.

Aromatic amines in the context of the present invention are in principal all compounds which have at least one aromatic ring, for example benzene or naphthalene, especially benzene, which aromatic ring is substituted by at least one substituted or unsubstituted amino function (amino group). The aromatic ring is preferably substituted by at least one unsubstituted amino function (—$NH_2$). The aromatic ring may optionally comprise at least one additional substituent, for example an alkyl group such as methyl, ethyl, propyl, or longer-chain alkyl substituents. Particular preference is given to preparing aniline in the process according to the invention. Aniline may optionally be substituted by one or two alkyl groups, especially methyl groups. More particularly, however, unsubstituted aniline is prepared.

In the process according to the invention, the reactants prepared are the corresponding aromatic nitro compounds (based on the aromatic amines). This means that, in the process according to the invention, the nitro groups (—$NO_2$) present in the reactant are replaced by the corresponding amino groups (substituents/—$NH_2$). Accordingly, in the process according to the invention, the corresponding aromatics comprising at least one nitro substituent can be used. These aromatic nitro compounds may optionally comprise at least one further substituent. Preferred reactants are consequently nitrobenzene, nitrotoluene or dinitrotoluene. Particular preference is given to using nitrobenzene as the reactant in the process according to the invention.

Catalytic hydrogenation in the context of the present invention means the reaction of the aromatic nitro compounds with hydrogen in the presence of a catalyst to give the corresponding aromatic amines. The catalytic hydrogenation can be performed by methods known to those skilled in the art. For example, the pressure may be 1 to 50 bar, preferably 2 to 20 bar, more preferably 2 to 10 bar. The hydrogenation temperature is, for example, 150 to 400° C., preferably 200 to 300° C., more preferably 270 to 300° C.

The catalyst used in the process according to the invention comprises copper as the (catalytically active) metal component (copper catalyst). The catalyst is additionally based on a support comprising silicon dioxide ($SiO_2$). The $SiO_2$ present in the support of the copper catalyst was prepared by wet grinding and subsequent spray drying. Expressed in other words, this means that, in the preparation of the support of the copper catalyst, a wet grinding step is carried out. The wet grinding step is followed by a spray drying step.

The catalyst used in the process according to the invention may comprise copper (concentration figures which follow calculated as CuO) in any desired concentrations. The catalyst preferably comprises copper in an amount of 15 to 40% by weight, especially in an amount of 25 to 35% by weight. The percentages by weight of copper and of any further metals present are based on the total catalyst weight, i.e. including the support material. Copper and any further metals present may be present in any desired oxidation states, for example in the 0 oxidation state (metallic copper) and/or in the +I and/or +II oxidation state in the form of copper oxides. The same applies to any further metals present.

As further metals, the copper catalyst may comprise at least one metal (as the pure element or in the form of a compound, for example as the oxide) selected from main group I, main group II, transition group VI and transition group II of the PTE. It is optionally possible for further metals known to the person skilled in the art from aniline preparation processes, for example palladium, nickel, cobalt or platinum, to be present in the copper catalyst. The copper catalyst preferably additionally comprises at least one metal selected from potassium (K), sodium (Na), barium (Ba), chromium (Cr), molybdenum (Mo), palladium (Pd), zinc (Zn), tungsten (W), nickel (Ni) or cobalt (Co). The copper catalyst more preferably additionally comprises at least one metal selected from potassium, barium or zinc. The additional metals may be present in the copper catalyst in any desired concentrations, though the sum of the weight of the further metal components is preferably less than the weight of the copper present in the catalyst. The sum of the additional metals present in the copper catalyst is preferably 1 to 10% by weight, especially 1 to 5% by weight.

Processes for preparing copper catalysts are known in principle to those skilled in the art. The copper and optionally the additionally present metals may firstly be applied to the finished support. This means that the support is first prepared as such, before copper and optionally at least one further metal are applied to the finished support. "Finished support" in the context of the present invention means that the individual catalyst particles are already (virtually) completely formed. A finished support is thus present after the wet grinding step and subsequent spray drying step. Copper and/or further metals are applied after the drying and/or calcining step of the finished support particles.

On the other hand, copper and/or the further metals can also be introduced into the catalyst preparation process as early as in the course of support preparation. The copper catalyst of the process according to the invention is preferably prepared by applying copper and optionally at least one further metal to the finished support comprising $SiO_2$. Methods for applying metals such as copper to a finished support are known to those skilled in the art. The application is preferably effected by impregnating the support with a solution comprising copper and optionally at least one further metal. Copper and the further metals can be added, for example, in the form of carbonate solutions, especially ammoniacal carbonate solutions, or nitrate solutions. The addition can be effected in portions for each metal component or else in one step.

The copper catalyst preferably has a surface area of 150 to 380 $m^2/g$. It is additionally preferred to use the copper catalyst as a fluidized bed catalyst (in a fluidized bed reactor).

The copper catalyst of the process according to the invention comprises a support, the support in turn comprising $SiO_2$ which has been prepared by wet grinding and subsequent spray drying. Wet grinding processes (wet grindings) for producing particles of particular size are known in principle to those skilled in the art. Wet grinding in the context of the present invention is understood to mean the comminution of already formed silicon dioxide ($SiO_2$) to particles of a particular size/diameter. The comminution is effected by grinding in a mill suitable therefor, for example a pin mill or a turbo mill, especially a stirred ball mill. This involves initially charging the silicon dioxide to be comminuted in a liquid. The silicon dioxide present in the liquid is also referred to as slurry. The slurry preferably has a solids content of 10 to 15% by weight and a pH of 5 to 10. It is preferably an $SiO_2$ suspension, especially an aqueous $SiO_2$ suspension.

The $SiO_2$ present in the slurry in the wet grinding can be prepared by processes known to those skilled in the art. The $SiO_2$ is preferably prepared by the sol-gel process (production of silica gel). For example, sodium silicate such as $Na_2SiO_3$ can be reacted with sulfuric acid to give $SiO_2$. The reaction product can be washed with aqueous ammonia solution or with carbon dioxide dissolved in water. The material obtained has coarse particles and is generally subsequently sent to a comminution process, especially a grinding process. In the context of the present invention, this is done in the form of wet grinding.

The $SiO_2$ particles produced in the wet grinding may have any desired sizes/diameters. The wet grinding preferably produces $SiO_2$ particles with an (average) diameter of 1 to 35 μm, especially 2 to 30 µm. The $SiO_2$ produced in the wet grinding and subsequent spray drying preferably has a surface area of 400 to 620 $m^2/g$.

The support of the copper catalyst preferably comprises more than 95% by weight, especially more than 98% by weight, of $SiO_2$, based on the support as such without taking account of the catalytically active metal components. The support is preferably free or substantially free of additives and/or binders. It is optionally possible, however, for additional additives, binders or other substances to be present in the support as well as $SiO_2$. These additional components can be added either before the wet grinding step, for example during the sol-gel process, or during or else after the wet grinding step. The copper catalyst may optionally also be used on a support mixture comprising $SiO_2$ and further support materials known to those skilled in the art, such as aluminum oxide.

The $SiO_2$ obtained in the wet grinding step can optionally be used directly as a support for the copper catalyst. Normally, the wet grinding step is followed by performance of an additional spray drying step and optionally a calcining step. The drying and/or calcining of $SiO_2$ which is obtained by grinding steps, especially wet grinding steps, is known to those skilled in the art. The drying step preferably removes the liquid which originates from the slurry by spraying. The drying step is preferably followed by performance of a calcining step. Calcining steps are preferably performed at temperatures of 150 to 300° C., especially 250 to 280° C. The calcining time is normally 1 to 5 hours.

In a preferred embodiment of the present invention, an aqueous alkali metal hydroxide solution is added to the $SiO_2$ during or after the wet grinding. Preference is given to adding an aqueous sodium hydroxide (NaOH) solution, for example in the form of a 25% solution. This is preferably performed after the wet grinding, i.e. to a slurry which already comprises $SiO_2$ particles of the desired size, preferably $SiO_2$ particles with a diameter of 1 to 35 µm. In particular, this step is carried out shortly before a drying step, especially a drying step by spraying of the slurry liquid.

In a further embodiment of the present invention, at least two fractions obtained by wet grinding are mixed with one another, the two fractions comprising $SiO_2$ particles with a different (average) diameter. The mixing operation may be followed, for example, by the addition of an aqueous alkali metal hydroxide solution and/or drying and calcining steps.

In one embodiment of the present invention, the above-described copper catalyst can be used in a fluidized bed reactor, in which case internals which divide the fluidized bed into a multitude of cells arranged horizontally and a multitude of cells arranged vertically in the fluidized bed reactor are provided. Such fluidized bed reactors are described, for example, in WO 2008/034770. In this case, a gaseous reaction mixture comprising the corresponding nitro compound and hydrogen is passed from the bottom upward through the copper catalyst in the fluidized bed reactor. The cell walls of the cells are gas-pervious and have orifices which ensure an exchange rate of the copper catalyst in vertical direction in the range from 1 to 100 liters/h per liter of reactor volume.

The orifices in the cell walls of the cells arranged in the fluidized bed reactor preferably ensure an exchange rate of the copper catalyst in vertical direction in the range from 10 to 50 liters/h per liter of reactor volume, and in horizontal direction of 0 or in the range from 10 to 50 liters/h per liter of reactor volume. It is additionally also preferred to configure the internals as cross-channel packings with bent gas-pervious metal sheets, expanded metal or fabric plies arranged parallel to one another in vertical direction in the fluidized bed reactor, with bend edges which form bend areas with a non-zero angle of inclination to the vertical, the bend areas of successive metal sheets, expanded metal or fabric plies having the same angle of inclination, but with the opposite sign, thus forming cells delimited in the vertical direction by constrictions between the bend edges. The angle of inclination of the pressure surfaces to the vertical is in the range from 10 to 80°, especially between 30 and 60°.

In a further embodiment, the catalyst is used in a fluidized bed reactor as described, for example, in DE-A 11 48 20 or DE-A 11 33 394.

In a further embodiment of the present invention, the process is performed in a fluidized bed reactor in which a gas distributor is installed. Such gas distributors are known to those skilled in the art; they are described, for example, in CN-A 1 634 860.

The aromatic amines prepared in the process according to the invention can optionally be subjected to one or more purifying steps after the catalytic hydrogenation. For example, the purification can be effected by distillation. Thus, the water present in the reaction can be removed by distillation from the resulting aromatic amine in the reaction mixture, in which case the water content of the organic amine can be lowered in a single distillation step to less than 20% by weight, based on the mixture of organic amine and water. The heat of reaction released in the hydrogenation can be used to heat the above-described distillation. The distillation column is preferably operated at an absolute top pressure of less than 1 bar. It is additionally also possible to remove any low boilers which occur by distillation.

Optionally, the aromatic amine (crude amine) obtained in the hydrogenation can be extracted with an aqueous alkali metal hydroxide solution, and then the aqueous and organic phases can be separated from one another. In this case, the concentration of the alkali metal hydroxide solution used and the temperature during the extraction are adjusted such that the aqueous phase constitutes the lower phase in the separation of the aqueous and organic phases. The extraction is preferably performed at temperatures of 30 to 50° C.

The invention is illustrated further by the examples which follow.

EXAMPLE 1

Support Preparation

Proceeding from waterglass and sulfuric acid, a silica hydrosol is prepared by spraying into individual droplets with a gel formation time of 1-15 seconds. The hydrosol droplets adopt a spherical shape and are taken up in water. They are then washed. The hydrogel spheres thus obtained comprise 14-20% by weight of $SiO_2$. The hydrogel spheres are then ground with addition of $H_2O$ in a stirred ball mill to give a slurry with a solids content of 13% by weight. The slurry is then mixed with 25% NaOH and then spray dried. Finally, the powder thus obtained is calcined at 260-280° C. for 4 h. The particles thus prepared have a microspheroidal form with the following features:
bulk density 470 $kg/m^3$
particle sizes 10-300 µm
BET surface area 480 $m^2/g$

EXAMPLE 2

Preparation of a Copper Catalyst 60 g of support from example 1 are initially charged in a rotary evaporator at oil bath temperature 120° C. To the support is added, in portions, a mixture of 179.02 g of ammoniacal copper carbonate solution, 1.74 g of potassium nitrate and 1.4 g of zinc nitrate. The catalyst prepared is dried and then calcined at 200-550° C. for 135 min (catalyst 1).

The analytical data of catalyst 1 are compiled in table 2 below:

TABLE 2

|  | Fines (%) | Abrasion (%) | BET surf. $m^2/g$ | Bulk density $kg/m^3$ |
|---|---|---|---|---|
| Catalyst 1 | 4.3 | 8.8 | 375 | 790 |

The abrasion rates are measured in a jet abrasion apparatus.

The abrasion test simulates the mechanical stresses to which a fluidized material (for example a catalyst) in a gas/solid fluidized bed is exposed, and gives an abrasion rate and a fines content which describes the durability.

The abrasion apparatus consists of a nozzle base (nozzle Ø=0.5 mm) which is connected to a glass tube in a gas- and solids-tight manner. Above the glass tube is fixed a steel tube with a conical widening, likewise in a gas- and solids-tight manner. The system is connected to the 4 bar compressed air network. A reducing valve lowers the pressure upstream of the system to 2 bar absolute.

60.0 g of catalyst are introduced into the system. The compressed air rate of the test performance is 350 l/h. The system itself is operated under atmospheric conditions (1 bar, 20° C.). Particle/particle and particle/wall collisions abrade and comminute the particles owing to the high gas velocity at the nozzle. The solids discharged pass through a pipe bend into a sleeve of filter paper (pore size 10-15 µm), and the cleaned gas flows into the laboratory waste air system.

The deposited solids (particles<20 µm) are weighed after one hour (defined as the fines content) and after 5 hours (defined as the abrasion).

EXAMPLE 3

Aniline Preparation

The performance of catalyst 1 is tested in continuous operation in a 5 l reactor [T=290° C., p=6 bar absolute, hydrogen: 2 m³ (STP)/h of $H_2.N_2$: 8 m³ (STP)/h, catalyst hourly space velocity 0.91 $kg_{MNB}/kg_{cat} \times h$]. Preheated nitrobenzene is pumped into the reactor by means of a two-substance nozzle and nebulized there at the nozzle orifice with a portion of the hydrogen stream.

With catalyst 1, a conversion of 100% and a selectivity of >99.5% over 11 cycles, 500 h in total, were achieved. After 11 cycles, the reaction was stopped, though the catalyst was still active.

The invention claimed is:

1. A process for preparing an aromatic amine, comprising:
hydrogenating, with a copper catalyst, a corresponding aromatic nitro compound,
wherein:
the copper catalyst comprises a support comprising $SiO_2$ obtained by wet grinding and subsequent spray drying,
the copper catalyst additionally comprises potassium and zinc,
the copper catalyst has a surface area of from 150 to 380 $m^2/g$,
the $SiO_2$ has a surface area of from 400 to 620 $m^2/g$,
the hydrogenating is performed at a pressure of 2 to 20 bar and a temperature of 200 to 300° C.,
the catalyst comprises copper in an amount of 15 to 40% by weight, and
the sum of the potassium and zinc and any additional metals present in the copper catalyst is 1 to 10% by weight.

2. The process of claim 1, wherein a copper content in the copper catalyst is from 25 to 35% by weight.

3. The process of claim 1, wherein the copper catalyst additionally comprises at least one additional metal selected from the group consisting of sodium, barium, chromium, molybdenum, palladium, tungsten, nickel, and cobalt.

4. The process of claim 3, wherein a content or sum of contents by weight of the at least one additional metal is less than a content by weight of copper in the copper catalyst.

5. The process of claim 1, wherein the aromatic amine is aniline.

6. The process of claim 1, wherein the copper catalyst is a fluidized bed catalyst.

7. The process of claim 1,
wherein the wet grinding produces $SiO_2$ particles and
an average particle diameter of the $SiO_2$ particles is from 1 to 35 µm.

8. The process of claim 1, wherein the wet grinding employs a slurry with a solids content of from 10 to 15%.

9. The process of claim 1, comprising addition of an aqueous alkali metal hydroxide solution during or after the wet grinding.

10. The process of claim 9, wherein the aqueous alkali metal hydroxide solution is an aqueous NaOH solution.

11. The process of claim 1, wherein the copper catalyst is obtained by a process comprising applying copper to the support comprising $SiO_2$.

12. The process of claim 11, wherein the applying comprises impregnating the support with a solution comprising copper.

13. The process of claim 11, wherein the copper catalyst is obtained by a process comprising applying at least one further metal to the finished support comprising $SiO_2$.

14. The process of claim of claim 13, wherein the applying comprises impregnating the support with a solution comprising the at least one further metal.

15. The process of claim 1, wherein the aromatic nitro compound comprises nitrobenzene, nitrotoluene, or dinitrotoluene.

16. The process of claim 1, further comprising purification after hydrogenation.

* * * * *

UNITED STATES PATENT AND TRADEMARK OFFICE
CERTIFICATE OF CORRECTION

PATENT NO. : 8,809,588 B2  
APPLICATION NO. : 13/320384  
DATED : August 19, 2014  
INVENTOR(S) : Lucia Königsmann et al.

Page 1 of 1

It is certified that error appears in the above-identified patent and that said Letters Patent is hereby corrected as shown below:

On the title page, Item (12) the Letters Patent Heading, and Item (75), the 1st Inventor's Last Name and 6th inventor's city are incorrect. Item (12) and (75) should read:

-- (12) United States Patent
 Königsmann, et al. --

-- (75) Inventors: Lucia Königsmann, Stuttgart (DE); Ekkehard Schwab, Neustadt (DE); Michael Hesse, Worms (DE); Christian Schneider, Mannheim (DE); Thomas Heidemann, Viernheim (DE); Celine Liekens, Antwerpen (BE); Jutta Bickelhaupt, Fraenkisch-Crumbach (DE); Dirk Theis, Ludwigshafen, (DE) --

Signed and Sealed this  
Sixteenth Day of December, 2014

Michelle K. Lee  
*Deputy Director of the United States Patent and Trademark Office*